(12) United States Patent
Schiffler et al.

(10) Patent No.: US 8,576,398 B2
(45) Date of Patent: Nov. 5, 2013

(54) CONCENTRATION MEASURING DEVICE, CONCENTRATION MEASURING ARRANGEMENT AND CONCENTRATION MEASURING METHOD

(75) Inventors: Ingo Schiffler, Freiburg (DE); Thomas Beyer, Freiburg (DE)

(73) Assignee: Sick AG, Waldkirch (DE)

( * ) Notice: Subject to any disclaimer, the term of this patent is extended or adjusted under 35 U.S.C. 154(b) by 57 days.

(21) Appl. No.: 13/439,407

(22) Filed: Apr. 4, 2012

(65) Prior Publication Data

US 2012/0257202 A1    Oct. 11, 2012

(30) Foreign Application Priority Data

Apr. 5, 2011    (EP) .................................. 11002848

(51) Int. Cl.
    *G01N 21/59*    (2006.01)
(52) U.S. Cl.
    USPC .......................................... 356/437; 356/440
(58) Field of Classification Search
    USPC ................................................ 356/432–440
    See application file for complete search history.

(56) References Cited

U.S. PATENT DOCUMENTS

| | | | |
|---|---|---|---|
| 5,303,036 A | | 4/1994 | McLachlan et al. |
| 7,405,827 B2 * | | 7/2008 | Keranen ........................ 356/432 |
| 2005/0270535 A1 * | | 12/2005 | Robertson et al. ............ 356/432 |
| 2009/0236524 A1 | | 9/2009 | Huebner et al. |
| 2010/0265492 A1 | | 10/2010 | Schroeder et al. |
| 2010/0283991 A1 * | | 11/2010 | Chrzan et al. .................... 356/51 |
| 2012/0055238 A1 * | | 3/2012 | Schiffler ...................... 73/61.41 |

FOREIGN PATENT DOCUMENTS

| WO | 99/13303 A1 | 3/1999 |
|---|---|---|
| WO | 2006/030059 A1 | 3/2006 |

* cited by examiner

*Primary Examiner* — Hoa Pham
(74) *Attorney, Agent, or Firm* — Nath, Goldberg & Meyer; Jerald L. Meyer; Sanjana Mangalagiri

(57) ABSTRACT

A concentration measuring device for determining a concentration of gas or particles in a measurement volume includes at least one housing having an opening for communication with the measurement volume, a light source for transmitting measurement light through the housing into the measurement volume, a light receiver for receiving the measurement light after its passage through the measurement volume and an evaluation unit which is designed for determining the concentration of gas or particles from the measurement light received at the light receiver. In accordance with the invention at least one body of solid material is arranged in the at least one housing such that the measurement light path largely passes through the at least one solid body within the housing, with the portion of the measurement light path within the at least one housing not passing through the at least one solid body having a specified total length.

20 Claims, 2 Drawing Sheets

CONCENTRATION MEASURING DEVICE, CONCENTRATION MEASURING ARRANGEMENT AND CONCENTRATION MEASURING METHOD

The invention relates to a concentration measuring device for determining a concentration of gas or particles in a measurement volume, to a concentration measuring arrangement with a measurement volume and such a concentration measuring device and to a concentration measuring method which can be performed using such a concentration measuring device.

BACKGROUND OF THE INVENTION

In known solutions for measuring concentrations of gas or particles in a measurement volume, concentration measuring devices are used which have a housing which can be flanged with an opening e.g. to a structure defining a measurement volume which contains a medium in which the concentration of a specific gas or of a specific type of particle should be determined.

DISCLOSURE OF THE INVENTION

A light source for transmitting measurement light through the housing into the measurement volume is provided for this purpose. The measurement light is received by a light receiver after its passage through the measurement volume, with the light receiver being able to be arranged e.g. in the same housing as the light transmitter or in a second housing which is likewise flanged with an opening to the structure defining the measurement volume. In the first-named case, a corresponding reflector which reflects the measurement light back in the direction of the light receiver after the first passage through the measurement volume is e.g. arranged at the oppositely disposed side of the measurement volume.

The concentration of gas or particles can be determined with the aid of an evaluation unit from the absorption of the measurement light on the path from the light transmitter to the light receiver.

The light transmitter, light receiver, evaluation unit and any optionally present optical elements such as lenses form an optical analyzer.

A frequent area of application of such concentration measuring devices is the determination of the oxygen concentration in a medium which is located in a measurement volume or which flows through a corresponding measurement volume. In the following, oxygen will frequently be specified as the gas to be measured, with corresponding concentration measuring devices, however, also being able to be provided and designed or used in an analogous manner for the concentration determinations of other gases.

It is desirable in this respect that only the oxygen concentration in this measurement volume is measured. Optical analyzers, however, have free light paths between the contained optical elements and are usually offset a little from the actual measurement volume to avoid high temperatures and contamination, in particular when hot gas or corrosive gas is in the measurement volume. The free paths (dead volumes) should—in the measurement of oxygen concentrations—be free of oxygen or the oxygen contained there must be removed from the measured value by calculation. It is finally necessary in many applications that the concentration measuring device is insulated from the gas to be measured in the measurement volume in order e.g. to allow the measurement of hot gases.

To obtain devices free of oxygen or dead volumes free of oxygen between the measurement volume and the actual optical analyzer, in known solutions flushing gases are used which have a different composition than the gas to be measured. With oxygen measuring devices, for example, the corresponding dead volume is thus flushed with nitrogen or another oxygen-free gas, e.g. water vapor.

Other solutions provide that the actual optical analyzer and the light conducting optical system are encapsulated for the long term with a permanent and oxygen-free gas filling or in a vacuum.

The flushing with oxygen-free gas is complex and expensive in this respect since the gases have to be procured, stored and prepared. The flushing in particular has to be monitored in safety-relevant applications. An encapsulation, on the other hand, brings along the risk of a leak.

Other approaches such as described in WO 2006/030059 attempt to keep the free paths between the light source, the lenses and the receiver as small as possible so that the oxygen still contained there is not significant. However, temperature problems can e.g. occur on the measurement of hot gas due to the proximity of the optical analyzer to the measurement volume which thereby arises.

Finally, provision is made in known solutions that the free stretches on the path of the light between the optical analyzer and the measurement volume are determined to deduct the oxygen contained there from a measured value by calculation, with there here being a risk of errors, in particular when the pressure or temperature in the measurement stretch and in the dead volumes are different.

A concentration measuring device for determining a concentration of gas or particles in a measurement volume is known from WO 2006/030059.

It is the object of the invention to provide a concentration measuring device or a concentration measuring arrangement and a concentration measuring method with whose aid the possible influence of the measurement light path outside the measurement volume on the concentration determination can be kept as small as possible.

This object is satisfied by a concentration measuring device for determining a concentration of gas or particles in a measurement volume, by a concentration measuring arrangement having a measurement volume and a concentration measuring device connected to the concentration measuring device and by a concentration measuring method wherein light is sent through at least one housing into the measurement volume and the concentration of gas or particles in the measurement volume is determined from measurement light received from the measurement volume. Dependent claims are directed to particular embodiments and aspects.

A concentration measuring device in accordance with the invention is characterized in that at least one solid body is arranged in the housing in which the light source and the light receiver are arranged or in the housings in which the light source or the light receiver are respectively arranged such that the measurement light path within the housing or housings largely passes through this solid. In this manner, the danger is eliminated or reduced that gas whose concentration should actually be determined in the measurement volume is located on the path between the light source, the light receiver and the measurement volume. The falsification by such a gas located on the path to the measurement volume is therefore minimized.

In this manner, an optical system which is reliably free of oxygen in accordance with safety aspects can be achieved over a specific distance between the light source and receiver respectively and the measurement volume e.g. on an oxygen measurement. Beam diameters of more than e.g. 4 mm can also be generated without problem to reduce the influence of dust in the measurement volume. The distance of the optical analyzer from the measurement volume can be increased to achieve a temperature decoupling without the risk of falsification due to gas on the path between the light source and receiver respectively and the measurement volume. In addition, a solid needs no monitoring, in contrast to flushing gas or liquid fillings, for example.

With a desired accuracy G for determining a concentration of gas or particles in a measurement volume having a measurement length ML, that part of the beam path of the measurement light which is located within the optical analyzer and does not pass through the at least one solid body is selected in accordance with the invention as shorter than a length SL which is determined by the formula $SL = 2 \cdot G \cdot ML/K$. Here K designates the concentration of gas or particles in the dead volumes of the optical analyzer which are defined in that they are located outside the measurement volume and in that there, the beam path does not pass through the at least one solid body. It is ensured in this manner that with a desired measurement accuracy G the contribution of the part of the light path not going through the solid is in every case smaller than twice the aimed for accuracy. The concentration measuring device in accordance with the invention is thus in particular suitable for determining a concentration of gas or particles in a measurement volume having a measurement length ML with a desired accuracy G.

The concentration K of gas or particles of the gas to be measured or of the particles to be measured such as is present in the dead volumes can—but does not have to—correspond to the concentration to be measured of the gas to be measured or of the particles to be measured in the measurement volume. E.g. it can differ due to different pressure and/or temperature conditions or because a dead volume has no communication with the volume.

The invention serves for a determination which is as accurate as possible of the gas to be measured or of the particles to be measured in the measurement volume and takes the fact into account that gas of the kind to be measured ("gas to be measured") or particles of the kind to be measured ("particles to be measured") can likewise be located in the dead volumes of the optical analyzer, but should have no influence or as little influence as possible.

The term "dead volumes" is used in the present text for those parts of the optical analyzer in which the beam path of the measurement light does not go through the at least one solid body and in which optionally gas or particles may be located which correspond to the gas to be measured in the measurement volume or to the particles to be measured in the measurement volume. Although the term is used in the plural as a rule, arrangements are not precluded and are included in which only one such dead volume is located.

With higher demands, other values for SL can also be fixed as the upper limit, for example $SL' = G \cdot ML/K$ or $SL'' = 0.5 \cdot G \cdot ML/K$.

The length SL is advantageously such that an accuracy of 0.1% is achieved with a measurement length ML of 1 m in the measurement volume and with a concentration within the dead volumes of the analyzer of 20%.

Percentage data as a rule relates to volume percent in the present text.

If therefore, e.g. in an oxygen measurement, an accuracy of 0.1% oxygen on a 1 m measurement stretch is to be achieved, a maximum length of the free light path of 10 mm is selected with an oxygen concentration within the dead volumes of the analyzer of 20%.

The solid of the at least one solid body can e.g. include a material which is otherwise also used for the optical elements such as are used in a manner known per se in the concentration measuring device (e.g. mirrors, lenses, beam splitters, filters, etc.). In this respect, the solid can, for example, be a glass body or a quartz glass body.

In particular a coherent light source, e.g. a laser light source, can be used as the light source in a concentration measuring device in accordance with the invention. In the present case, the term "light" is not only used for visible light, but also for electromagnetic waves from other energy ranges, e.g. infrared or ultraviolet.

The at least one solid body can e.g. also be designed so that measurement light is not reflected back on itself at any optical surface so that interference is avoided. This can e.g. be realized by mirror-coated surfaces or obliquely standing surfaces. The optical surfaces at the end of the solid body can e.g. also be used to split a measurement light beam if the reflected portion is used, on the one hand, and the transmitted portion is used, on the other hand. Internal reflections at curved surfaces can be utilized for the beam shaping.

Provision is made in an embodiment that the solid is arranged such that the geometry of the beam path of measurement light propagating therein substantially corresponds to the geometry of a corresponding beam path without such a solid. The solid therefore has no light conducting effect or other optical effect and only replaces the free light path.

Provision is advantageously made for an embodiment in which the solid body includes regions which act like optical elements, that is in particular have properties of lenses or reflectors, that the geometry of the beam path in those regions which do not act like optical elements substantially corresponds to the geometry of a corresponding beam path without the solid.

Optically effective regions such as they are mentioned above can be integrated into a corresponding solid body, can include a further solid body which is, for example, bonded on, clipped on or pressed on or can be formed by an independent further solid.

A concentration measuring arrangement in accordance with the invention has a measurement volume and a concentration measuring device in accordance with the invention connected thereto, preferably flanged thereto. Such a concentration measuring arrangement is in particular suitable to determine the concentration of a gas or of particles with a desired accuracy G when the portion of the beam path not passing through the at least one solid body has a total length within the optical analyzer, but outside the measurement volume, which is smaller than a length SL which is determined in accordance with the formula $SL = 2 \cdot G \cdot ML/K$, where ML designates the length of the light path in the measurement volume and K the concentration of gas or particles of the gas to be measured in the portion of the beam path not belonging to the measurement volume, that is in the dead volumes of the optical analyzer.

With a concentration measuring method in accordance with the invention for determining a concentration of gas or particles in a measurement volume, light is sent through at least one housing into the measurement volume, with the light in the housing being sent largely through at least one body of a solid material and the portion of the beam path not passing through the solid having a total length which is smaller than a length SL, where $SL = 2 \cdot G \cdot ML/K$. Here G is the desired accuracy of the concentration determination on a measurement length ML of the measurement volume at a concentration K of the gas to be measured in the beam path within the optical analyzer, but outside the measurement volume. In this respect, the concentration method in accordance with the invention for determining a concentration of gas or particles in a measurement volume having a measurement length ML with a desired accuracy G is suitable in particular when a gas concentration K is present in the dead volumes of the analyzer.

The special advantages and preferred embodiments of the concentration measuring method in accordance with the invention result in an analog manner from the above descriptions of the special embodiments and advantages of the concentration measuring device in accordance with the invention.

A concentration measuring device in accordance with the invention, a concentration measuring arrangement in accordance with the invention and a respective concentration measuring method in accordance with the invention can be used particularly advantageously to determine the oxygen concentration in a measurement volume. It is of special advantage in particular with such an application if no measurement result falsification due to a beam path outside the measurement volume can be present in a dead volume in which oxygen (e.g. as part of the air) is also present. It can nevertheless be ensured by the invention that a sufficient spacing of the optical analyzer from the measurement volume can be observed, e.g. to ensure a temperature decoupling.

The claimed invention provides a formula for the length SL based on an accuracy G to be obtained when a measurement length ML is used and a concentration K is present of the gas to be measured in the beam path within the optical analyzer, but outside the measurement volume.

The invention will be explained in detail in the following with reference to the schematic Figures which represent embodiments of a concentration measuring device in accordance with the invention.

DETAILED DESCRIPTION OF THE INVENTION

Figure 1:
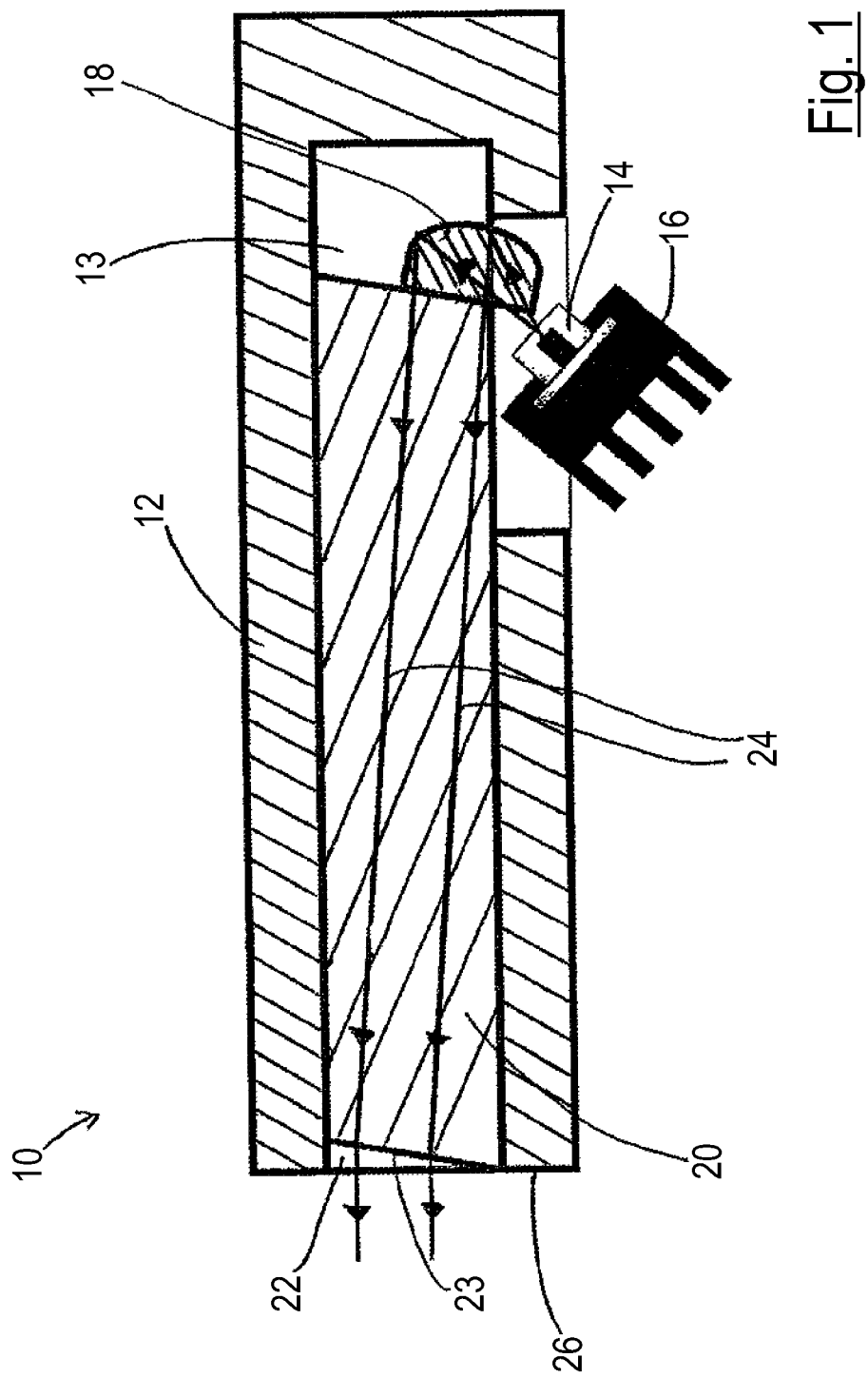
FIG. 1 shows an embodiment of a concentration measuring device in accordance with the invention such as can be flanged to a structure defining a measurement volume, in a schematic representation.

FIG. 1 shows a part of an embodiment of a concentration measuring device in accordance with the invention in a schematic representation in cross-section. A housing 12, e.g. a stainless steel housing, has a hollow space 13 in which a glass body 20 is located. A glass body 18 which is shaped so that it deflects measurement light 24 which is produced by a laser 14, for example by a laser diode, such that it is directed through the glass body 20 is adhesively bonded to the glass body 20 at the rear. The arched side of the glass body 18 can e.g. be mirror-coated for this purpose. Reference numeral 16 designates e.g. a heat sink or a circuit board or similar for the electrical contacting of the laser 14 which can be formed by a laser diode.

As shown, the glass body 20 fills the hollow space 13 in the housing 12 almost completely in a manner such that the light path of the measurement light 24 runs almost completely through glass. Only a small region 22 of the measurement light path is not filled with glass in this embodiment. The boundary surfaces of the space 22 are selected in the embodiment shown such that no reflection of the measurement light 24 takes place at the surface 23. At the end 26, the concentration measuring device 10 is connected, for example flanged, in a suitable manner known per se to a structure defining a measurement volume, not shown, in which the gas is present whose concentration should be determined.

The measurement light in this embodiment is sent through the measurement volume, not shown. A corresponding arrangement can be located on the other side of the measurement volume, with no laser being provided there, but rather a light receiver, e.g. a photodiode. This enables the measurement of the absorption and, from this, the concentration of the gas in the measurement volume in a manner known per se. The wavelength of the light used is in this respect e.g. selected such that it is in particular absorbed by the constituents of the gas whose concentration should be determined.

In an alternative embodiment, a photodiode is provided together with the laser 14 on the same side of the measurement volume, so that measurement light can be detected which is reflected back in the measurement volume or is reflected back at a reflector at the end of the measurement volume in a manner known per se.

The concentration can be determined from the intensity of the measurement light received at the light receiver. In this respect, the absorption of the measurement light can e.g. be evaluated which depends on the concentration of the absorbing material. It is generally also possible to measure scattered light which provides information on the concentration or quantity of gas in the measurement volume.

For use in the determination of a concentration with an accuracy G (e.g. 0.1%) with a measurement length ML (e.g. 1 m) determined by the dimension of the measurement volume and with a concentration K of the gas to be measured such as is present within the dead volumes of the optical analyzer (e.g. 20%), the total length SL of the light path in the housing 12 which does not pass through the glass body 20 or the glass body 18 is selected such that it is shorter than a length SL which is determined using the following formula:

$$SL = 2 \cdot G \cdot ML/K.$$

In the example shown, in particular the region 22 is therefore correspondingly selected.

On a measurement in which the absorption in a measurement volume is used for the concentration determination, the measurement length ML corresponds, for example, to the diameter of the measurement volume which is radiated through (with a simple radiation) or to twice the diameter (with a double radiation, e.g. in a reflection arrangement).

Figure 2:
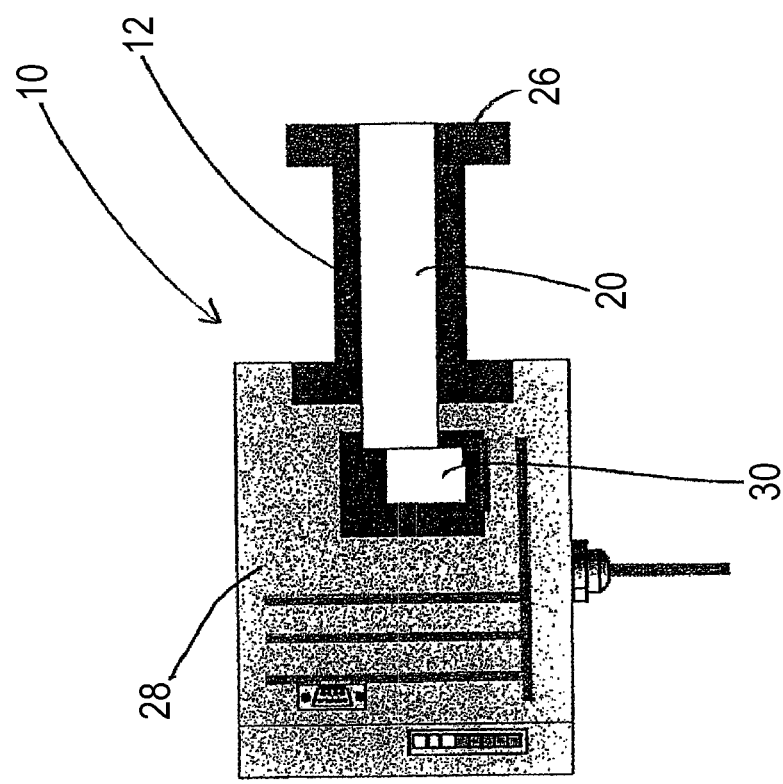
FIG. 2 shows another embodiment of a concentration measuring device in accordance with the invention.

FIG. 2 shows another embodiment in a schematic representation. The same elements or elements having the same function are marked with the same reference numerals. Here, an optical analysis unit 30 is shown which includes, in a manner not shown, a laser diode as the light source and a photodiode as the receiver. The light is sent through the glass body 20 in the direction of a measurement volume, not shown, which is flanged to the surface 26 of the stainless steel body 12. Light reflected in the measurement volume is transmitted back by the glass body 20 in the direction of the optical analyzer 30 and is detected by the photodiode there. A conclusion on the concentration of a gas in the measurement volume can be drawn from the quantity of reflected light.

A connection housing 28 is shown schematically here in which the connection and operating electronics for the optical analyzer are located.

REFERENCE NUMERAL LIST

10 concentration measuring device
12 housing 13 hollow space
14 laser diode
16 connection board
18 optical glass body
20 glass body
22 dead volume
23 glass body surface
24 beam path
26 housing surface for flanging
28 connection housing
30 optical analyzer

The invention claimed is:

1. A concentration measuring device for determining a concentration of gas or particles in a measurement volume, comprising at least one housing having an opening for communication with the measurement volume; a light source for transmitting measurement light through the at least one housing into the measurement volume; a light receiver for receiving the measurement light after its passage through the measurement volume, wherein the light receiver is arranged either in the same housing as the light transmitter or in a second housing having an opening for communication with the measurement volume; and an evaluation unit which is designed to determine the concentration of gas or particles from the measurement light received at the light receiver, wherein at least one body of solid material is arranged in the at least one housing such that the measurement light path largely passes through the at least one solid body within the at least one housing, with the portion of the measurement light path within the at least one housing not passing through the at least one solid body having a total length which is smaller than a length SL, where SL=2GML/K and G is the desired accuracy of the concentration determination on a measurement length ML in the measurement volume for a gas to be measured or particles to be measured within the dead volumes occurring in the housing having a concentration amounting to K.

2. A concentration measuring device in accordance with claim 1, wherein the portion of the beam path of the measurement light not passing through the at least one solid body has a total length which is smaller than a length SL which is selected such that an accuracy of 0.1% is achieved with a measurement length ML of 1 m in the measurement volume and a concentration of the gas to be measured or of the particle concentration to be measured within the dead volumes occurring in the housing of 20%.

3. A concentration measuring device in accordance with claim 1, wherein the portion of the beam path of the measurement light not passing through the at least one solid body has a total length which is smaller than 20 mm.

4. A concentration measuring device in accordance with claim 1, wherein the at least one solid body is such that the geometry of the beam path of measurement light propagating therein substantially corresponds to the geometry of a corresponding beam path without the solid.

5. A concentration measuring device in accordance with claim 1, wherein the at least one solid body comprises regions which act like optical elements.

6. A concentration measurement device in accordance with claim 5, wherein the at least one solid body comprises regions having lens properties or reflection properties.

7. A concentration measuring device in accordance with claim 5, wherein the at least one solid body is such that the geometry of the beam path of measurement light propagating therein in those regions which do not act like optical elements substantially corresponds to the geometry of a corresponding beam path without the solid.

8. A concentration measuring device in accordance with claim 1, wherein the at least one solid body is formed by at least one glass body.

9. A concentration measuring device in accordance with claim 1, wherein the evaluation unit is designed to determine the concentration of gas or particles from the absorption of the measurement light on the path from the light transmitter to the light receiver.

10. A concentration measuring arrangement having a measurement volume and a concentration measuring device connected thereto in accordance with claim 1.

11. A concentration measuring arrangement in accordance with claim 10, wherein the concentration measuring device is flanged to the measurement volume.

12. A concentration measuring method for determining a concentration of gas or particles in a measurement volume, wherein light is sent through at least one housing into the measurement volume and the concentration of gas or particles in the measurement volume is determined from measurement light received from the measurement volume, and wherein the light within the housing is directed largely through at least one body of solid material, with the portion of the measurement light path within the at least one housing not passing through the at least one solid body having a total length which is smaller than a length SL, where SL=2GML/K and G is the desired accuracy of the concentration determination on a measurement length ML in the measurement volume for a gas to be measured or particles to be measured within the dead volumes occurring in the housing having a concentration amounting to K, which is carried out using a concentration measuring device in accordance with claim 1.

13. A concentration measuring device in accordance with claim 1, wherein the portion of the beam path of the measurement light not passing through the at least one solid has a total length which is smaller than 10 mm.

14. A concentration measuring device in accordance with claim 1, wherein the portion of the beam path of the measurement light not passing through the at least one solid body has a total length which is smaller than 5 mm.

15. A concentration measuring method for determining a concentration of gas or particles in a measurement volume comprising the steps,
sending light through at least one housing into the measurement volume; and
determining the concentration of gas or particles in the measurement volume from measurement light received from the measurement volume;
wherein the light within the housing is directed largely through at least one body of solid material, with the portion of the measurement light path within the at least one housing not passing through the at least one solid body having a total length which is smaller than a length SL, where SL=2GML/K and G is the desired accuracy of the concentration determination on a measurement length ML in the measurement volume for a gas to be measured or particles to be measured within the dead volumes occurring in the housing having a concentration amounting to K.

16. A concentration measuring method in accordance with claim 15, wherein the portion of the beam path not passing through the at least one solid body has a total length which is smaller than a length SL which is selected such that an accuracy of 0.1% is achieved with a measurement length ML of 1 m in the measurement volume and a concentration of the gas to be measured or of the particle concentration to be measured within the dead volumes occurring in the housing of 20%.

17. A concentration measuring method in accordance with claim 15, wherein the portion of the beam path not passing through the at least one solid body has a total length which is smaller than 20 mm.

18. A concentration measuring method in accordance with claim 15, wherein the concentration of gas or particles in the measurement volume is determined from the absorption of the measurement light.

19. A concentration measuring method in accordance with claim 15, wherein the portion of the beam path not passing through the at least one solid body has a total length which is smaller than 10 mm.

20. A concentration measuring method in accordance with claim 15, wherein the portion of the beam path not passing through the at least one solid body has a total length which is smaller than 5 mm.

* * * * *